March 21, 1939. A. F. J. BAUR Plant Pat. 319
CARNATION
Filed July 22, 1938
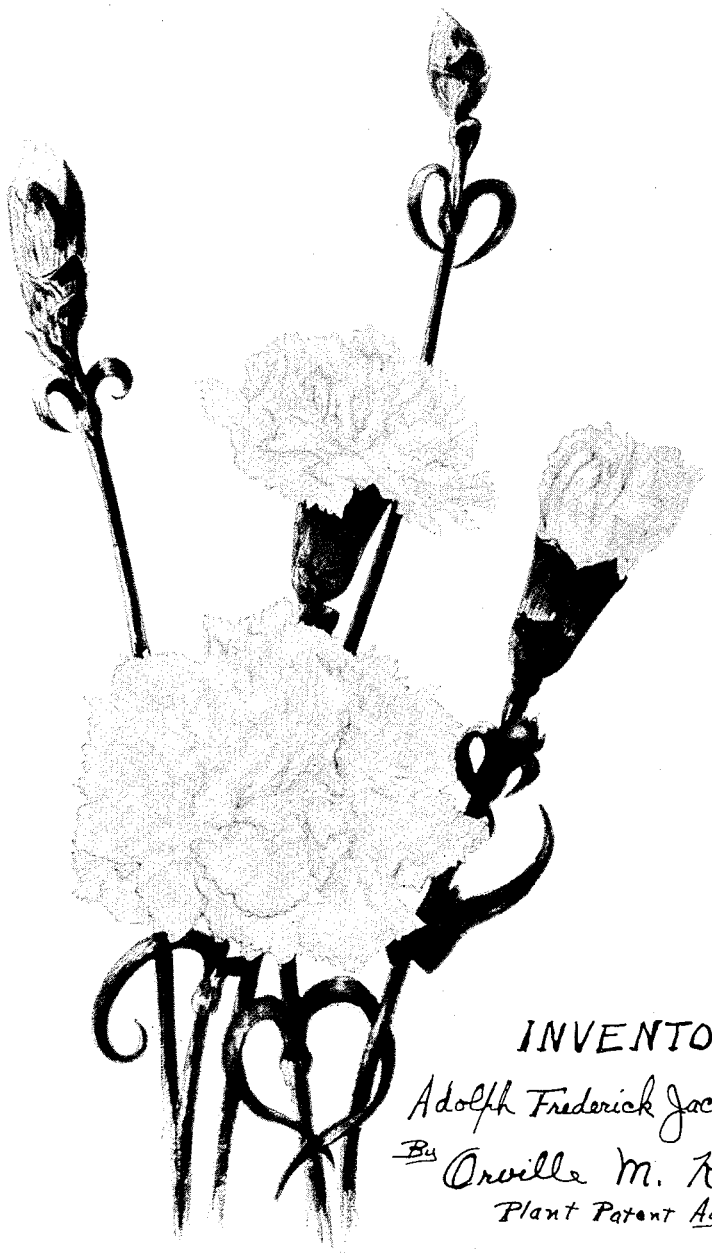
INVENTOR
Adolph Frederick Jacob Baur
By Orville M. Kile
Plant Patent Agent Patented Mar. 21, 1939 Plant Pat. 319

UNITED STATES PATENT OFFICE

319

CARNATION

Adolphe Frederick Jacob Baur, Indianapolis, Ind., assignor to Baur-Steinkamp and Company, Incorporated, Indianapolis, Ind.

Application July 22, 1938, Serial No. 220,795

1 Claim. (Cl. 47—60)

My present invention relates to improvements in fragrant carnations of the type known as perpetual blooming or greenhouse forcing carnations. The object of my invention is to produce a new and improved deep pink carnation of the type indicated. This variety is the result of definite breeding efforts and came from a cross of the seed parent which produced the varieties Patrician and Pink Treasure, with another of my unnamed but numbered seedlings.

The new variety has been asexually reproduced for several years and its characteristics are apparently established.

The original illustrations accompanying this application show a front view and side view of a fully opened flower, three buds in varying stages of development, together with a portion of the stems and leaves—all as nearly natural as they could be shown. It must be understood, however, that it is impossible for the artist to show the beauty of sheen of this new variety.

Color references are to Ridgway's Color Standards and Nomenclature, except where lack of plate reference makes it obvious that the ordinary dictionary term is intended.

The following is a more detailed description of this new variety of carnation.

*The plant*

The plant is a very vigorous grower, attaining a height of three feet or more, and producing good length of stem at the beginning of the blooming season. It is very free flowering, and disease resistant.

Foliage:

Ample. Heavy. Long and narrow. The third pair of leaves from the blossom averages 4 inches long and slightly over ¼ inch wide for each leaf.

*Color.*—Empire Green (Plate XXXII) overlaid with gray bloom.

Stems:

Long and strong, retaining their length throughout the season. Same color as the foliage.

*The flower*

Blossom:

*Size.*—Medium, averaging 3¼ inches across.

*Form.*—High, well-filled center.

*Color.*—The dominant color effect is Rose Color (Plate XII), which appears at a glance to be uniformly spread over the petal. Upon closer examination it is found that the central portion of the petal is high-lighted by a bright sheen. The under side of the entire flower is considerably lighter than the upper side and the portion which is enclosed in the calyx is white or greenish-white.

Petalage:

The number of petals in April is from 45 to 55.

*Petals.*—Irregularly serrated and moderately crinkled. Substantial but silky in texture. Outer petals measure 1¼ inches wide and 1¼ inches from top to claw or shank, their entire length being 2½ inches.

Calyx:

Exceedingly strong, entirely free from splitting. Consists of a single tube with five lobes. Light Bice Green (Plate XVII).

Bracts:

Strong and large. Same color as stems.

Fragrance:

Pleasing, mild.

Longevity:

Very good keeping qualities.

*Reproductive organs*

Ovary:

Seed pod or ovary is of medium size, three-lobed.

Pistils:

Two curved pistils—white at the base and pink-tinted at the top—surmount the ovary and extend a length of 1½ inches above the ovary.

Stamens:

About a dozen white stamens surround the ovary, only a few of them being topped by anthers.

Anthers:

Medium in size. Light yellow.

*Comparison*

The variety which most resembles my new variety is one introduced by me in 1924 under the name of Betty Lou, but the present variety is an improvement over Betty Lou in several respects.

This variety has a bright sheen which Betty Lou does not possess. This makes it readily distinguishable from Betty Lou when the two varieties are displayed side by side. My new variety grows somewhat taller and gives better length of stem in the early part of the blooming season. It is more free in flower production than is Betty Lou. It is disease resistant whereas Betty Lou is seriously lacking in this quality.

Having thus disclosed my invention, what I claim is:

The new variety of carnation herein shown and described, characterized particularly by its strong stems having unusually good length in the early part of the blooming season; its strong, non-splitting calyx, its vigorous growth and disease resistance; and its abundant production of deep pink (Rose Color) flowers with distinctive bright sheen.

ADOLPHE FREDERICK JACOB BAUR.